United States Patent [19]

Moore

[11] Patent Number: 4,569,784

[45] Date of Patent: Feb. 11, 1986

[54] PREPARATION OF A GEL HAVING GAS TRANSPORTING CAPABILITY

[75] Inventor: Robert E. Moore, Wilmington, Del.

[73] Assignee: Adamantech, Inc., Marcus Hook, Pa.

[21] Appl. No.: 313,124

[22] Filed: Oct. 20, 1981

Related U.S. Application Data

[63] Continuation-in-part of Ser. No. 209,238, Nov. 17, 1980, abandoned.

[51] Int. Cl.$^4$ .............................................. B01J 13/00
[52] U.S. Cl. ................................. 252/315.1; 252/312; 252/314; 514/789; 514/944
[58] Field of Search .................... 252/312, 314, 315.1; 424/177, 352; 514/789

[56] References Cited

U.S. PATENT DOCUMENTS

| | | | |
|---|---|---|---|
| 3,277,013 | 10/1966 | Gianladis | 252/312 X |
| 3,778,381 | 12/1973 | Rosano et al. | 252/312 X |
| 3,823,091 | 7/1974 | Samejima et al. | 252/312 |
| 3,850,753 | 11/1974 | Chibata et al. | 435/248 |
| 3,911,138 | 10/1975 | Clark, Jr. | 436/15 X |
| 3,993,581 | 11/1976 | Yokoyama et al. | 252/312 |
| 4,105,798 | 8/1978 | Moore et al. | 435/1 X |
| 4,166,006 | 8/1979 | Hertl et al. | 435/244 |
| 4,299,728 | 11/1981 | Cormier et al. | 252/312 X |
| 4,366,169 | 12/1982 | White | 424/DIG. 13 |

*Primary Examiner*—Richard D. Lovering
*Attorney, Agent, or Firm*—J. Edward Hess; Donald R. Johnson; Stanford M. Back

[57] ABSTRACT

An inert, water-immiscible inert organic liquid having gas transport properties, water and a suitable emulsifying agent are formed into a stable gel by emulsifying a mixture of the same, concentrating the emulsion to form a gel phase and a liquid phase, and separating the two phases. The resulting gel can be used as an ointment or cosmetic for skin irritations or wounds, or as a coating in industrial applications where extended contact of a surface with a gas, such as oxygen, is desired. Fluorocarbons or low viscosity silicone oils are suitable organic liquid components of the gels.

12 Claims, No Drawings

PREPARATION OF A GEL HAVING GAS TRANSPORTING CAPABILITY

RELATED APPLICATION

This application is a continuation-in-part of Ser. No. 209,238 filed Nov. 17, 1980 and abandoned as of the filing date accorded this application.

BACKGROUND OF THE INVENTION

This invention relates to a process for preparing a gel composition based on an inert organic liquid having gas transporting capability. The invention also relates to the resulting gel composition, which gel has a variety of medical, cosmetic, industrial and other uses.

Many inert organic liquids are known which have gas transporting capabilities, that is, have high solubility for gases such as oxygen, nitrogen, carbon dioxide, the inert gases, and mixtures of gases including air. Among the many classes of inert organic liquids having such properties are water immiscible, liquid fluorocarbons and low viscosity silicone oils. These classes of liquids are described in U.S. Pat. No. 3,850,753 issued Nov. 26, 1974 to Chibata et al for the culturing of aerobic microorganisms. However, the patent does not mention emulsions or gel formulation therewith.

Other perfluorocarbons, emulsions thereof and their properties are described in the following U.S. Pat. Nos.: 4,220,606, R. E. Moore, Sept. 2, 1980; 4,143,079, R. E. Moore, Mar. 3, 1979; 4,105,798, R. E. Moore et al., Aug. 8, 1978; 4,041,086, Moore et al., Aug. 9, 1977; 3,911,138, L. C. Clark, Jr., Oct. 7, 1975; 3,962,439, K. Yokoyama et al., June 8, 1976; 3,993,581, K. Yokoyama et al., Nov. 23, 1976; 4,187,252, R. J. Lagow et al., Feb. 5, 1980; 4,110,474, R. J. Lagow et al., Aug. 29, 1978; and 3,641,167, Moore et al., Feb. 8, 1972. In U.S. application Ser. No. 52,041 filed June 25, 1979, now abandoned, by David C. White, superseded by Ser. No. 228,642 filed Jan. 26, 1981, now U.S. Pat. No. 4,366,169, a method of treating wounds, such as a burn, is disclosed wherein the burn is contacted with a liquid perfluorocarbon, directly or supported on a sponge, or in the form of a foam, spray or gel. There is no disclosure in the White application of any specific gel composition or of any process for preparing a gel composition.

The information contained in the aforementioned patents is incorporated herein by reference.

Techniques are known for separating various particulate materials from aqueous media in which they are formed or treated. For example, U.S. Pat. No. 2,107,839 describes isolation in dry powder form of the therapeutic agent derived from the natural latex of the Lactuca plant, by allowing the emulsion to break by standing, and then filtering or centrifuging to separate the aqueous solution containing the active constituent.

Further, a variety of gels are known which are produced from aqueous suspensions by precipitation, decantation, filtration (including membrane filtration) and centrifugation. The products are commonly isolated as dry materials and are called "gels" apparently because they revert to a semi-solid, somewhat plastic or swollen state upon contact with water. They exhibit high porosity and are used for a variety of purposes, depending on their origin, porosity and swellability. Among such materials are the gelatin-carboxymethyl cellulose complexes of U.S. Pat. No. 2,824,092; the soybean proteinate hydrogels of U.S. Pat. No. 3,218,307; the gelatinous flocculent obtained by fermenting a natural polysaccharide and then centrifuging, as in U.S. Pat. No. 3,096,293; hydroxy-lower alkyl ethers of galactomannans produced as stable, dry hydrocolloids by filtration and centrifugation, as in U.S. Pat. No. 3,326,890; the dry, agarose gels of U.S. Pat. No. 3,527,712; and the silica gels produced as in U.S. Pat. Nos. 3,346,507 and 3,560,400.

None of these patents, however, teach or suggest concentration of an emulsion accompanied by formation of a gelatinous material, nor preparation of a gelatinous material containing an inert, water-immiscible organic liquid gas transporting agent.

SUMMARY OF THE INVENTION

In accordance with the present invention, it has now been found that a gel composition can be prepared by (a) combining an inert, water-immiscible organic liquid having gas transport capabilities, water, and a suitable emulsifying agent, emulsifying the combined materials, concentrating the emulsion to form a gel phase and a liquid phase, and separating the liquid from the gel. The resulting gel is a stable composition which can be used, for example, as an ointment, salve or unguent, in the treatment of skin irritations or wounds, or of any condition requiring a gas such as oxygen. Gas transporting agents in gel form have the advantage over emulsions of far greater gas transport capability per unit volume since a large proportion of the non-gas transporting material, i.e., the water, is removed as a consequence of the present invention.

DETAILED DESCRIPTION

The term "gel" as used herein means a semisolid, apparently homogeneous, substance that may be elastic and jelly-like (as gelatin) or more or less rigid. Contrary to the teachings of the patents set forth above, the "gels" of this invention are not reducible to dry, particulate, porous form, nor do they exhibit any appreciable degree of swelling upon contact with water. "Gel" therefore is used herein in the more general sense of a gelatinous or jelly-like character.

"Perfluorocarbon" as used herein refers to a substantially fluorinated or completely fluorinated material which is generally but not necessarily a liquid at ambient temperature and pressure and which has the ability to transport gases such as oxygen and carbon dioxide.

"Substantially fluorinated" in this specification means that most of the hydrogen atoms of a compound have been replaced by fluorine atoms, such that further replacement does not substantially increase the gas transport capability of the material. It is believed that this level is reached when at least about 80–90% of the hydrogen atoms have been replaced by fluorine atoms. In the aforementioned U.S. Pat. Nos. 3,911,138 and 4,105,798, the ability to transport oxygen is related to the solubility of a gas such as oxygen in the materials. These patents suggest that the perfluorinated materials will absorb 10–100 cc of oxygen per 100 cc of material at 25° C. and 760 milliliters of mercury. However, it is preferred that at least 95% of the hydrogen atoms have been replaced, more preferably at least 98% and even more preferably, 100%.

Fluorinated materials suitable for use in this invention include those which are broadly described as cyclic perfluorohydrocarbons or derivatives thereof. Examples are chemically inert $C_9$–$C_{18}$ polycyclic compounds such as bicyclononanes (e.g., bicyclo[3.3.1]nonane, 2,6- dimethyl-bicyclo[3.3.1]nonane or 3-methylbicyclo[3.3.1]nonane), adamantane, methyl and dimethyladamantane, ethyl and diethyladamantane, tetrahydrodicyclopentadiene, methyl and dimethylbicyclooctanes, ethylmethyladamantane, ethyldimethyladamantane, tetrahydrobinor-S, methyldiadamantane, triethyladamantane, trimethyldiadamantane, pinane, camphane, 1,4,6,9-dimethanodecalin, bicyclo[4.3.2]undecane, bicyclo[5.3.0]decane and the like, or any mixtures thereof. Other examples include perfluorotributyl amine, perfluoro-2-butyltetrahydrofuran, perfluoro-2-butylfuran, perfluoro-n-heptane, perfluoronaphthalene, perfluoro-1-methyl-napthalene, perfluoro-n-methylmorpholine and perfluoro-1-methyldecaline and perfluoroethers such as the 1,2,2,2-tetrafluoromethyl ether of perfluoro (2,5,8-trimethyl-3,6,9-trioxa-1-dodecanol).

Certain of the fluorine atoms of the foregoing materials may be substituted by other halogen atoms such as bromine. Included among these compounds, are, for example, monobrominated compounds such a 1-bromopentadecafluoro-4-isopropylcyclohexane, 1-bromotridecafluorohexane, 1-bromo-pentadecafluorooctane and 1-bromopentadecafluoro-3-isopropylcyclopentane, or dibrominated derivatives thereof.

Perfluorinated $C_8$ or lower materials and up to $C_{18}$ or higher materials, included partially brominated analogs thereof, as well as mixtures of various different perfluorocompounds can be used in this invention.

Those of the foregoing fluorinated compounds which are solid at ambient temperature can be dissolved in a suitable solvent or in other perfluorocarbons which are liquid at ambient temperatures, and the resulting mixture can be used to form the emulsion and gel of the invention. "Liquid" in this specification when describing the fluorocarbons therefore means either a fluorocarbon which is per se liquid at ambient temperatures or a solution of a solid fluorocarbon in a fluorocarbon solvent.

Silicone oils useful in this invention, such as those mentioned in U.S. Pat. No. 3,850,753, should have a viscosity of from about 0.65 to about 15 centipoise, such as the silicone oil "DC-200-1CD" manufactured by Dow Corning Corporation having a molecular weight of 316, specific gravity 0.85, and an oxygen solubility of 100 ml/100 ml. liquid at 25° C. Other silicone fluids available from the Dow-Corning Corporation having utility in this invention are generally described as "DC-200" fluids. Chemically, the silicone oils are polydimethyl siloxanes, and are also known as liquid methyl silicones. Similar silicone fluids are available from the General Electric Company.

In the first step of preparing the gels, the inert organic, gas transporting liquid is emulsified in water in the presence of an emulsifying agent. The emulsifying agent is selected such that when admixed with the water and the organic liquid, effective emulsification and stability of the gel will result. The emulsifying agent should be compatible with the organic liquid and have no adverse effect when the gel is applied, for example, to the human skin.

Although nonionic emulsifiers are preferred, because they are effective in hard or soft water and are not pH dependant, ionic emulsifiers can also be used, whether anionic, cationic or amphoteric.

Suitable nonionic emulsifiers include alkylphenoxypolyethoxyethanols having alkyl groups of about seven to eighteen carbon atoms and 1 to 60 or more oxyethylene units, such as heptylphenoxypolyethoxyethanols, octylphenoxypolyethoxyethanols, methyloctylphenoxypolyethoxyethanols, nonylphenoxypolyethoxyethanols, dodecylphenoxypolyethoxyethanols, and the like; polyethoxyethanol derivatives of methylene linked alkylphenols; sulfur-containing agents such as those made by condensing 1 to 60 or more moles of ethylene oxide with nonyl, dodecyl, tetradecyl, t-dodecyl, and the like mercaptans or with alkylthiophenols having alkyl groups of six to fifteen carbon atoms; ethylene oxide derivatives of long-chain carboxylic acids, such as lauric, myristic, palmitic, oleic, and the like or mixtures of acids such as are found in tall oil containing 1 to 60 oxyethylene units per molecule; analogous ethylene oxide condensates of long-chain alcohols, such as octyl, decyl, lauryl, or cetyl alcohols; ethylene oxide derivatives of etherified or esterified polyhydroxy compounds having a hydrophobic hydrocarbon chain, such as sorbitan monostearate containing 1 to 60 oxyethylene units; also, ethylene oxide condensates of long-chain or branched-chain amines, such as dodecylamine, hexadecylamine, and octadecylamine, containing 1 to 60 oxyethylene groups; and block copolymers of ethylene oxide and propylene oxide comprising a hydrophobic propylene oxide section combined with one or more hydrophilic ethylene oxide sections.

Examples of useful anionic emulsifiers include the ordinary soaps such as the alkali metal, ammonium and alkanolamine salts of fatty acids including sodium oleate, potassium palmitate, ammonium stearate, ethanolamine laurate, and the like, as well as rosin and dehydrated rosin acid soaps, and the synthetic saponaceous materials including the higher aliphatic sulfates and sulfonates such as sodium lauryl sulfate, sodium cetyl sulfate, the sodium salts of sulfonated paraffin oils, the sodium salts of dodecane-1-sulfonic acid, octadecane 1-sulfonic acid, and the like; the alkaryl sulfonates such as the sodium alkyl aryl sulfonates, e.g., sodium isopropyl benzene sulfonate, sodium isopropyl napthalene sulfonate; and the alkali metal salts of sulfonated dicarboxylic acid esters and amides such as sodium dioctyl sulfosuccinate, sodium N-octadecyl-sulfonsuccinamide, sulfonated or sulfated alkyl phenoxyethoxyethanols having from 1 to 50 oxyethylene units per molecule in which the alkyl group has from 4 to 18 carbon atoms, such as hexyl, n-octyl, t-octyl, lauryl, hexadecyl, and octadecyl, and the like.

Cationic emulsifiers include stearamidopropyl-dimethyl-beta-hydroxyethyl ammonium dihydrogen phosphate, stearamidopropyldimethyl-beta-hydroxyethyl ammonium nitrate, stearoguanamine, stearoguanamine ethylene oxide reaction products, octadecylamine salts of octadecyl carbamic acid and octadecyl guanamine salts of octadecyl carbamic acid reacted with ethylene oxide, octadecylamine tetraethylene glycol, rosin amine ethylene oxide reaction products, and the like. Also included are undecylimidazoline and reaction products with ethylene oxide and propylene oxide; oleylaminodiethylamine hydrochloride; condensation products of fatty acids and degraded proteins; monostearylethylenediamine trimethylammonium sulfate; alkyl benzene imidazolines, cetyl pyridinium bromide, octadecyl pyridinium sulfate or chloride, octadecylmethylene pyridinium acetate; laurylureaethylene oxide; methyl sulfate of dimethyl octadecyl sulfonium; condensates of halohydrins and amines, polyamines and ammonia; alkyl phosphonium compounds, alkyl phosphonium ethylene oxide condensates, rosin amines condensed with ethyl oxide and propylene oxide; cetyl dimethylbenzyl ammonium chloride, distearyl dimethyl ammonium chloride, stearyl dimethylbenzyl ammonium chloride, n-alkyl dimethylbenzyl ammonium chloride, methyl dodecylbenzyl trimethyl ammonium chloride, methyl dodecyl xylene bis(trimethylammonium chloride), cetyl trimethyl ammonium bromide, and the like.

Amphoteric emulsifiers include the sodium salt of N-coco beta aminopropionate, N-coco beta aminopropionic acid, disodium N-lauryl beta-iminodipropionate, dicarboxylic coconut derivative diethanolamine salt, dicarboxylic palmitic derivative sodium salt, C-cetyl betaine, and N-lauryl betaine.

Fluorine containing surfactants of all types are useful, whether ionic or nonionic. Among the anionic types may be mentioned ammonium perfluoroalkyl sulfonates, potassium perfluoroalkyl sulfonates, potassium fluorinated alkyl carboxylates, and ammonium perfluoro alkyl carboxylates. The fluorinated alkyl esters are examples of nonionic types. The foregoing and other fluorine containing surfactants are commercially available, such as surfactants FC-93, FC-95, FC-128, FC-143, FC-430 and F-431 sold by 3M Company.

Naturally occurring emulsifiers or derivatives thereof are also useful. These include the alginates, cellulose derivatives such as methyl cellulose and carboxymethyl cellulose, water soluble gums such as gum arabic and gum tragacanth, the phospholipids (such as lecithin), and the sterols.

Preferred emulsifying agents are the nonionic emulsifiers, Pluronic (trademark) F-68 and Pluronic F-108, and yolk-phospholipid. The Pluronic emulsifiers are polyoxyethylenes and polyoxypropylenes available from Wyandotte-BASF. Typically, the emulsifier (whether nonionic or ionic) is used in an amount up to about 10 wt.% of the total emulsion composition, or up to about 5 wt.% based on the water used to form the emulsion. Greater amounts can be used if desired. The emulsifiers can be used singly or in combination provided they are ionically compatible.

The amounts and proportions of inert, organic, gas transporting liquid water and emulsifying agent used to form the emulsion and gel can vary over a wide range. Generally, the amounts of each ingredient will be such as to form an emulsion and can be readily determined by one skilled in the art without undue experimentation. However, the preferred concentration of the organic liquid is in the range of from about 1 wt.% to about 70 wt.%, more preferably from about 10 to about 50 wt.% on total composition.

In another aspect of the present invention, the gel can be treated to contain more oxygen than would otherwise result. One such technique is to contact the organic liquid prior to combining it with the other material, with additional oxygen. For example, the organic liquid prior to emulsification may be subjected to an environment of 100% oxygen at a pressure equal to or greater than 760 mm Hg. Alternatively, the resulting gel is subjected to an environment of 100% oxygen which may be at a pressure equal to or greater than 760 mm Hg.

The mixture of organic liquid, water and emulsifying agent is emulsified by any conventional means of agitation, for example, by hand stirring, aeration, propeller agitation, turbine agitation, colloid milling, homogenizing, high-frequency or ultrasonic oscillation (sonication), and the like. In most instances emulsification is effective at ambient temperature. However, with some of the foregoing agitation means, excess heat may be generated during the formation of the emulsion and/or gel and will be removed by known means, e.g., cooling jacket. The amount of mechanical energy input from the various agitation means can vary substantially depending on, for example, the amount of material being worked and the equipment used.

In the second step of preparing the gels of the invention, the emulsion is concentrated to form a gel phase and a liquid phase. High speed centrifugation ("ultracentrifugation"), for example at about 10,000 to 20,000 rpm, is effective for this purpose, the selection of speed being dependent on the proportion of organic liquid in the emulsion (the less organic liquid, the greater the speed). The result is a clear, supernatant liquid and a paste-like solid (the gel phase) which falls to the bottom of the vessel.

In the third step, the gel phase and liquid phase are separated, as by settling, evaporation, decantation, or filtration such as pressure filtration or vacuum filtration. Separation may be partial or complete, depending on what further processing is required. For example, if it is desired to admix other adjuvants with the gel at this point, such as antimicrobial agents, pharmaceuticals, hermectants, perfumes, colorants, or other additives known to the cosmetic chemist, it may be preferable to leave some of the liquid in contact with the gel. On the other hand, if immediate packaging or use is contemplated, complete separation of the liquid may be desirable.

The foregoing description of the second and third steps is a sequential concentration and separation process. These steps may also be effected simultaneously by microfiltration (also known as "ultrafiltration"). However, microfiltration is effective only for emulsions of relatively coarse particle size, of the order of more than 1 micron, since most commercial microfiltration membrances have an apparent pore diameter of 1 micron down to about 0.002 micron. Thus, if the emulsion particles are very fine, they may pass through the microfiltration membrane and will not be separated. Since many of the emulsions of this invention have particle sizes in the range of from about 0.1 to about 10 microns, microfiltration is a practical method of simultaneously concentrating the emulsion to form a gel and separating the gel from the resulting supernatant liquid phase. Suitable microfiltration membranes include products available from the Millipore Company and Amicon Corporation as described, for example, in U.S. Pat. Nos. 3,615,024 and 3,856,569.

Generally, when it is desired to simultaneously form the gel and separate the gel from the aqueous phase, a coarse emulsion particle size is desirable. Such emulsions are formed when the ingredients are utilized in the following proportions:
inert organic liquid: 10–50 vol.%
surfactant: 2–25 wt.%
water: 25–90 wt.%

The proportions may vary outside these ranges depending on the character of the inert organic liquid and surfactant.

Pressure or vacuum filtering or decantation can be used in conjunction with microfiltration, if desired. Pressure filtration is preferred over vacuum filtration due to a tendency to foaming during vacuum filtration.

If desired, an antimicrobial material such as an antibacterial agent and/or an antibiotic agent can be incorporated into the gels of the invention. The antibacterial agent counteracts aerobic bacteria which might multiply in the presence of the gel since the gel can contain large amounts of oxygen. Examples of suitable antibacterial agents include quinoline carboxylic acids, nitrofurans and sulfonamides. Suitable agents are those which do not affect the gel or ones not affected by the gel. Examples of suitable antibiotic agents include aminoglycosides, ansamacrolides, chloramphenicol and its analogues, lincosaminides, macrolides, nucleosides, oligosaccharides, peptides, phenazines, polyenes, polyethers, tetracyclines, and others. The foregoing agents are described in greater detail in Encyclopedia of Chemical Technology, Vol. 2, pages 752–1036 and Vol. 3, pages 7–78, both 3rd Edition. The aforementioned agent can be incorporated into the gel at any step in the preparation thereof, for example, by addition to a liquid ingredient prior to the emulsification (e.g., dissolving in the water), by dispersion in the emulsion during or after emulsification, or by blending with the gel after separation.

The resulting gel can be used as an ointment applied to the skin of higher mammals including humans, for treatment of wounds, bruises or irritations. The gel may also be formed or incorporated into a dressing and the dressing applied to the skin. "Dressing" as used herein includes any material suitable for contacting (including a wound) with the gel and maintaining the gel in such contact, such as gauze, bandages, surgical wrappings, and the like. The following examples illustrate several embodiments of the invention, but without intent to limit the scope thereof, except as set forth in the appended claims.

EXAMPLE 1

Four grams (2 cc) of F-tributylamine (perfluorotributylamine) and 18 cc of water containing 5 wt.% of Pluronic F68 emulsifying agent were placed in a test tube. The perfluorocarbon was evenly dispersed in the water by sonication. The test tube containing the milk-like emulsion was then centrifuged at 10,000 rpm for 10 minutes. The result was a clear supernatant liquid and a paste-like solid (gel) at the bottom. The clear liquid was poured from the tube leaving behind the gel. The gel was removed from the tube with a spatula to another container. The gel had the appearance of petroleum jelly and weighed 5 grams.

Ethanol, 5 cc, was added to the gel. Four grams of F-tributylamine, the amount used to form the emulsion initially, separated out as a clear liquid layer from the water-ethanol layer, indicating that the gel contained 80% by weight of fluorocarbon.

The foregoing procedure was repeated, except for the use of ethanol, and the separated gel was kept in a clear, wide-mouth jar. After 75 days no visible change was noted in the physical appearance of the gel, such as separation of the perfluorocarbon from the water, thus indicating that the gel was stable.

EXAMPLE 2

Pluronic F-68 surfactant, 1.35 g., was added to 25.65 g. water. To this aqueous mixture was added 3 cc. (6 g.) of F-tributylamine. The resulting composition was sonicated to form an opalescent emulsion of relatively coarse particle size (about 1–10 microns average particle size). The emulsion was filtered under about 25 psig. nitrogen pressure through a Millipore (trademark) microporous membrane of 0.45 micron apparent pore size. A gel formed and remained on the filter. The gel was readily transferrable to a storage container.

EXAMPLE 3

The preparative technique of Example 2 was repeated in all essential respects except for substitution of F-trimethylibicyclononane for the F-tributylamine. A gel of substantially equivalent appearance was obtained.

EXAMPLE 4

Substantially as described in Example 1, an emulsion was prepared by forming a solution containing 23.5 cc of water and 5 wt.% Pluronic F-68 emulsifier, adding 2.5 cc of General Electric Silicone Oil SF 96-50, and sonicating to a milky-white emulsion. The silicone oil has a viscosity of 50 c St, a specific gravity of 0.963, a flash point of 460° F. and a pour point of −67° F. The emulsion was then centrifuged at 14000 rpm for 20 minutes, whereupon a white, pasty gel separated. The separated fluid was then decanted from the gel.

I claim:
1. A method for preparing a gel, comprising:
  (a) admixing an inert, water-immiscible organic liquid having gas transporting capability, water, and an emulsifying agent under conditions of agitation and in proportions effective to form an emulsion;
  (b) concentrating the emulsion to form a gel phase and a liquid phase; and
  (c) separating all or a portion of the liquid phase from the gel phase.
2. The method of claim 1 wherein the organic liquid is a fluorocarbon or a low viscosity silicone oil.
3. The method of claim 1 wherein the concentrating and separation steps are effected sequentially.
4. The method of claim 3 wherein the concentrating step is effected by centrifugation.
5. The method of claim 1 wherein the concentrating and separating steps are effected simultaneously.
6. The method of claim 5 wherein the concentrating and separation steps are effected by passing the emulsion through a microfilter.
7. The method of claim 1 wherein an antimicrobial agent is incorporated into the gel during or after the formation thereof.
8. The method of claim 1 wherein oxygen is introduced into the organic liquid prior to the completion of step (c).
9. The method of claim 1 wherein oxygen is introduced into the gel after separation of the liquid phase therefrom.
10. The method of claim 1 wherein the organic liquid is a fluorocarbon.
11. The method of claim 10 wherein the fluorocarbon is a perfluorocarbon.
12. The method of claim 1 wherein the organic liquid is a low viscosity silicone oil.

* * * * *